US009862951B2

(12) United States Patent
Zeng et al.

(10) Patent No.: US 9,862,951 B2
(45) Date of Patent: Jan. 9, 2018

(54) RNA INTERFERENCE-BASED THERAPEUTIC AGAINST ANTHRAX

(71) Applicant: Texas Tech University System, Lubbock, TX (US)

(72) Inventors: Mingtao Zeng, El Paso, TX (US); Maria T. Arevalo, El Paso, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 14/898,179

(22) PCT Filed: Jun. 12, 2014

(86) PCT No.: PCT/US2014/042047
§ 371 (c)(1),
(2) Date: Dec. 14, 2015

(87) PCT Pub. No.: WO2014/201202
PCT Pub. Date: Dec. 18, 2014

(65) Prior Publication Data

US 2016/0145627 A1 May 26, 2016

Related U.S. Application Data

(60) Provisional application No. 61/834,946, filed on Jun. 14, 2013.

(51) Int. Cl.
*C12N 15/113* (2010.01)
*C07K 16/28* (2006.01)

(52) U.S. Cl.
CPC .......... *C12N 15/1138* (2013.01); *C07K 16/28* (2013.01); *C07K 2317/34* (2013.01); *C07K 2317/76* (2013.01); *C12N 2310/14* (2013.01); *C12N 2320/30* (2013.01)

(58) Field of Classification Search
CPC .............. C12N 2310/14; C12N 15/111; C12N 15/1131; C12N 15/1132; C12N 15/1138; C12N 15/62; C12N 15/63; C12N 15/635; C12N 15/902; C12N 2320/11; C12N 2320/30; C12N 2330/10; C12N 2501/999; C12N 2506/02; C12N 2740/16022; C12N 5/0606; C12N 5/0695; A61K 48/00; C07K 14/005; C07K 16/28; C07K 2317/34; C07K 2317/76
See application file for complete search history.

(56) References Cited

U.S. PATENT DOCUMENTS 7,601,351 B1 10/2009 Rosen et al.
2003/0143204 A1 7/2003 Lewis et al.

FOREIGN PATENT DOCUMENTS

WO 2004013313 A2 2/2004
WO 2012174160 A1 12/2012

OTHER PUBLICATIONS

Scobie et al PNAS Apr. 29, 2003 vol. 100 No. 9 , pp. 5170-5174.*
Chaudhary, A. et al. 'TEM8/ANTXR1 Blockade Inhibits Pathological Angiogenesis and Potentiates Tumoricidal Responses against Multiple Cancer Types', Feb. 14, 2012, Cancer Cell, vol. 21, pp. 212-226.
Li, G. et al, 'The inhibition of the interaction between the anthrax toxin and its cellular receptor by an anti-receptor monoclonal antibody', Aug. 7, 2009, Biochemical and Biophysical Research Communications, vol. 385, pp. 591-595. Abstract.
Bonuccelli, G. et al., 'ATR/TEM8 is highly expressed in epithelial cells lining Bacillus anthracis' three sites of entry: 'implications for the pathogenesis of anthrax infection', Feb. 2, 2005, Am J Physiol Cell Physiol , vol. 288, pp. C1402-C1410.
International Search Report and Written Opinion PCT/US2014/042047 [ISA/AU] dated Aug. 27, 2014.

* cited by examiner

*Primary Examiner* — Padmavathi Baskar
(74) *Attorney, Agent, or Firm* — Edwin S. Flores; Daniel J. Chalker; Chalker Flores, LLP

(57) ABSTRACT

The present invention includes siRNAs and antibodies that block the interaction between TEM8 and/or CMG2 cell surface proteins and anthrax toxin and methods of treating anthrax exposure with the same.

4 Claims, 3 Drawing Sheets

RNA INTERFERENCE-BASED THERAPEUTIC AGAINST ANTHRAX

CROSS-REFERENCE TO RELATED APPLICATIONS

This application claims priority to, and is the National Stage of International Application No. PCT/US2014/042047 filed on Jun. 12, 2014 and claims the priority of U.S. Provisional Patent Application Ser. No. 61/834,946, filed on Jun. 14, 2013, the contents of which are incorporated by reference herein in their entirety.

TECHNICAL FIELD OF THE INVENTION

The present invention relates in general to the field of strategies to treat anthrax that is caused by *Bacillus anthracis* infection, and more particularly, to novel RNAi-based therapeutics against anthrax toxins.

BACKGROUND ART

Without limiting the scope of the invention, its background is described in connection with alternative treatments against *Bacillus anthracis* infection or anthrax toxin exposure.

Inhalational anthrax is a leading bioterrorist threat and is fatal when left untreatedi. An anthrax vaccine has been licensed for human use (AVA or Biothrax, Emergent Biosolutions, Rockville, Md.), but the required immunization schedule is complicated, requiring six doses over 18 months followed by annual booster vaccinations. Post-exposure treatment for inhalational anthrax includes 60-day antibiotic therapy with a one-dose vaccination of AVA shortly after exposure, however, this treatment is unreliable at later stages of infection when large amounts of anthrax toxins have been produced.

*Bacillus anthracis* is the etiological agent responsible for anthrax. *B. anthracis* is a gram-positive, rod-shaped bacterium capable of forming stable and easily dispersible spores that can be developed and used as a bioweapon. Alveolar macrophages will ingest the *B. anthracis* spores following exposure via inhalation and transport these spores to draining lymph nodes where they germinate and produce virulence factors: a poly-D-glutamic acid capsule surrounding the vegetative form of the bacterium and toxins.

DISCLOSURE OF THE INVENTION

In one embodiment, the present invention includes a method of treating an anthrax infection in a subject in need of such treatment wherein an siRNA is provided to a subject that targets the cell surface expression of a TEM8 cell surface protein; wherein the siRNA is administered to said subject in a quantity effective to reduce anthrax toxin binding to cells in the subject. In one aspect, the siRNA specific for TEM8 is administered for the treatment of an anthrax infection of the respiratory tract. In another aspect, the siRNA specific for TEM8 is administered for the treatment of cutaneous anthrax infections. In another aspect, the siRNA specific for TEM8 is administered for the treatment of an anthrax infection of the gastrointestinal tract.

In one embodiment, the present invention includes a method of treating an anthrax infection in a subject in need of such treatment wherein an siRNA is provided to a subject that targets the cell surface expression of a CMG2 cell surface protein; wherein the siRNA is administered to said subject in a quantity effective to reduce anthrax toxin binding to cells in the subject. In one aspect, the siRNA specific for CMG2 is administered for the treatment of an anthrax infection of the respiratory tract. In another aspect, the siRNA specific for CMG2 is administered for the treatment of cutaneous anthrax infections. In another aspect, the specific for CMG2 is administered for the treatment of an anthrax infection of the gastrointestinal tract.

In one embodiment, the present invention includes a method of treating an anthrax infection in a subject in need of such treatment wherein an antibody is provided to a subject that blocks the interaction between the TEM8 cell surface protein and anthrax toxin; wherein the antibody is administered to said subject in a quantity effective to reduce anthrax toxin binding to cells in the subject. In one aspect, the antibody specific for TEM8 is administered for the treatment of an anthrax infection of the respiratory tract. In another aspect, the antibody specific for TEM8 is administered for the treatment of cutaneous anthrax infections. In another aspect, the antibody specific for TEM8 is administered for the treatment of an anthrax infection of the gastrointestinal tract.

In one embodiment, the present invention includes a method of treating an anthrax infection in a subject in need of such treatment wherein an antibody is provided to a subject that blocks the interaction between the CMG2 cell surface protein and anthrax toxin; wherein the antibody is administered to said subject in a quantity effective to reduce anthrax toxin binding to cells in the subject. In another aspect, the antibody specific for CMG2 is administered for the treatment of an anthrax infection of the respiratory tract. In another aspect, the antibody specific for CMG2 is administered for the treatment of cutaneous anthrax infections. In another aspect, the antibody specific for CMG2 is administered for the treatment of an anthrax infection of the gastrointestinal tract. In another aspect, the antibody that blocks the binding of anthrax toxin to TEM8. In another aspect, the antibody that blocks the binding of anthrax toxin to CMG2.

DESCRIPTION OF THE DRAWINGS

For a more complete understanding of the features and advantages of the present invention, reference is now made to the detailed description of the invention along with the accompanying figures and in which:

FIGS. 2A and 2B show that siRNA-targeted silencing of CMG2 and evaluation of anthrax LeTx toxicity.

FIG. 3 shows an evaluation of anthrax LeTx toxicity to Raw 264.7 cells in the presence of anti-CMG2 antibody.

DESCRIPTION OF EMBODIMENTS

Figure 1:
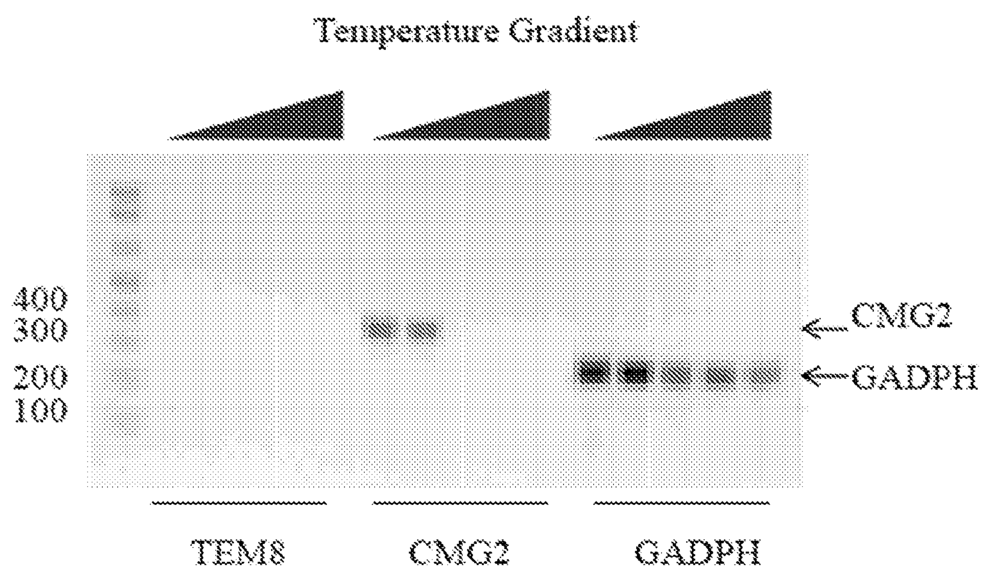
FIG. 1 shows the level of Anthrax toxin receptor mRNA expression in Raw264.7 macrophage as determined by RT-PCR.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as “a”, “an” and “the” are not intended to refer to only a singular entity, but include the general class of which a specific example may be used for illustration. The terminology herein is used to describe specific embodiments of the invention, but their usage does not delimit the invention, except as outlined in the claims.

The present invention includes nucleic acids that facilitate gene silencing via RNAi to downregulate or silence one or more transcriptionally active genetic regions that are directly or indirectly associated with the modulation of cell surface receptors.

As used herein, the term “RNA interference” refers to a process in which a double-stranded RNA molecule changes the expression of a nucleic acid sequence with which the double-stranded or short hairpin RNA molecule shares substantial or total homology. While not being bound by theory, the mechanism of action may include, but is not limited to, direct or indirect down regulation of the expression of the TEM8 and/or CMG2 cell surface receptor genes, decrease in TEM8 and/or CMG2 mRNA. The term “RNAi” includes an RNA sequence that elicits RNA interference, which can also be transcribed from a vector. Also used herein, the terms “short hairpin RNA” or “shRNA” refer to an RNA structure having a duplex region and a loop region that may be used to target the TEM8 and/or CMG2 genes, in which the RNAis are expressed initially as shRNAs. Both shRNA and RNAi are encompassed by the present invention.

As used herein, the term “RNAi expression cassette” refers to a cassette having at least one promoter that drives the transcription of the RNAi, which can also be followed by a termination sequence or unit. In some instances, a vector for use with the present invention may include multiple promoters upstream from the RNAi expression cassette. Thus, the terms “RNAi expression construct” or “RNAi expression vector” refer to vectors that include at least one RNAi expression cassette that targets the TEM8 and/or CMG2 genes.

Often, RNAi is optimized by using identical sequences between the target and the RNAi, however, RNA interference can be found with less than 100% homology. If there is less than 100% homology, e.g., 99%, 98%, 97%, 96%, or even 95%, 94%, 93%, 92%, 91% or even 90%, the complementary regions must be sufficiently homologous to each other to form the specific double stranded regions. The precise structural rules to achieve a double-stranded region effective to result in RNA interference have not been fully identified, but approximately 70% identity is generally sufficient. Accordingly, in some embodiments of the invention, the homology between the RNAi and TEM8 and/or CMG2 genes is at least 70%, 80%, 85%, 90%, or even 95% nucleotide sequence identity, so long as the cell surface expression of TEM8 and/or CMG2 is significantly lowered.

A common consideration for designing RNAi for targeting TEM8 and/or CMG2, is the length of the nucleic acid or the insert of a vector, for example, it is known that 17 out of 21 nucleotides is sufficient to initiate RNAi, but in other circumstances, identity of 19 or 20 nucleotides out of 21 may be required. While not being bound by theory, greater homology is commonly used in the central portion of a double stranded region than at its ends.

The RNA expression products of the RNAi expression cassette lead to the generation of a double-stranded RNA (dsRNA) complex for inducing RNA interference and thus down-regulating or decreasing expression of the TEM8 and/or CMG2 genes.

The term “homology” refers to the extent to which two nucleic acids are complementary. There may be partial or complete homology. A partially complementary sequence is one that at least partially inhibits a completely complementary sequence from hybridizing to a target nucleic acid and is referred to using the functional term “substantially homologous.” The degree or extent of hybridization may be examined using a hybridization or other assay (such as a competitive PCR assay) and is meant, as will be known to those of skill in the art, to include specific interaction even at low stringency.

The inhibition of hybridization of the completely complementary sequence to the target sequence may also be examined using a hybridization assay involving a solid support (e.g., Southern or Northern blot, solution hybridization and the like) under conditions of low stringency. Low stringency conditions may be used to identify the binding of two sequences to one another while still being specific (i.e., selective). The absence of non-specific binding may be tested by the use of a second target that lacks even a partial degree of complementarity (e.g., less than about 30% identity). In the absence of non-specific binding, the probe will not hybridize to the second non-complementary target and the original interaction will be found to be selective.

Low stringency conditions are generally conditions equivalent to binding or hybridization at 42° C. in a solution consisting of 5×SSPE (43.8 g/l NaCl, 6.9 g/l $NaH_2PO_4$—$H_2O$ and 1.85 g/l EDTA, pH 7.4), 0.1% SDS, 5×Denhardt's reagent (50×Denhardt's contains per 500 ml: 5 g Ficoll (Type 400, Pharmacia), 5 g BSA (Fraction V; Sigma) and 100 micrograms/ml denatured salmon sperm DNA); followed by washing in a solution comprising 5×SSPE, 0.1% SDS at 42° C. when a probe of about 500 nucleotides in length is employed.

The art knows that numerous equivalent conditions may be employed to achieve low stringency conditions. Factors that affect the level of stringency include: the length and nature (DNA, RNA, base composition) of the probe and nature of the target (DNA, RNA, base composition, present in solution or immobilized, etc.) and the concentration of the salts and other components (e.g., formamide, dextran sulfate, polyethylene glycol). Likewise, the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, inclusion of formamide, etc.).

As used herein, the term “gene” refers to a functional protein, polypeptide or peptide-encoding unit. As will be understood by those in the art, this functional term includes both genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated.

As used herein, the term “vector” is used in reference to nucleic acid molecules that transfer DNA segment(s) from one cell to another. The vector may exist in a state independent of the host cell chromosome, or may be integrated into the host cell chromosome.

*B. anthracis* secretes two binary toxins: (1) lethal toxin (LeTx), which cleaves mitogen-activated protein kinase kinases and leads to cell lysis, and (2) edema toxin (EdTx), which elevates intracellular cyclic adenosine monophosphate levels leading to swelling or edema. Both toxins have protective antigen (PA) in common, which is bound to either lethal factor (LF) or edema factor (EF). PA is responsible for host cell receptor binding and internalization of toxin complexes, binding to either of two identified anthrax toxin receptors: tumor endothelial marker 8 (TEM8) and capillary morphogenesis protein 2 (CMG2).

Upon infection of macrophages, *B. anthracis* spores germinate with the concomitant release of the three anthrax toxins: PA, EF, and LF. PA binds to two anthrax receptors (ANTXR1/TEM8) and anthrax toxin (ANTXR2/CMG2); followed by cleavage of PA and formation of a heptameric pore that binds EF or LF. These toxins combine to form edema toxin (EF+PA, EdTx) and lethal toxin (LF+PA, LeTx), which are translocated into the cytosol. The activities of LeTx and EdTx result in proinflammatory cytokine over secretion, cell shock and death, and malfunction of the host immune system. Therefore, it is critical to block the entry of anthrax toxins into the cytosol as well as overproduction of proinflammatory cytokines such as IL-1β and IL-18. Thus, anti-TEM8 and CMG2 siRNAs were used to inhibit the expression of the two toxin receptors on the cell surface, and to block the expression of the μ subunit of the heterotetrameric adaptor AP-1, which is essential for the endocytosis of anthrax toxins.

Anthrax spores can be aerosolized and dispersed as a bioweapon. Post-exposure treatment for inhalational anthrax is available, but unreliable at later stages of infection when high levels of anthrax toxins are present. Anthrax toxins enter cells via two identified anthrax toxin receptors: tumor endothelial marker 8 and capillary morphogenesis protein 2. The present inventors demonstrate herein the ability to block entry of anthrax toxins into macrophages by silencing anthrax toxin receptors using RNAi technology. Results show that silencing of capillary morphogenesis protein 2 using targeted siRNAs provides almost complete protection against cytotoxicity and death induced by anthrax lethal toxin as determined by viability assay. The same results were obtained by pre-binding cells with specific antibody prior to treatment with anthrax lethal toxin. Thus, the inventors identified capillary morphogenesis protein 2-targeted RNAi technology as a potential life-saving therapy following infection with anthrax.

The present invention demonstrates that silencing or blocking anthrax toxin receptor via targeted-siRNAs or neutralizing antibodies protects against anthrax LeTx-induced cell death in murine macrophages. Effective siRNA-targeted silencing of anthrax toxin receptor expression to prevent entry of these toxins into host cells and subsequent cytotoxicity could provide for post-exposure prophylaxis viable for both early and late stage anthrax infections.

Anthrax toxin receptor expression in the Raw 264.7 murine macrophage cell line. Transcript expression of the two anthrax receptors, TEM8 and CMG2, was evaluated in the Raw 264.7 cell line using RT-PCR methods. TEM8, CMG2, and GADPH murine gene amplifications were based on previously described methods that were optimized here for maximum amplification using annealing temperature gradient PCR (FIG. 1). Optimal amplification of murine CMG2 and GADPH genes was achieved at an annealing temperature of 55° C. However, TEM8 transcript was not detectable.

FIG. 1 shows the level of Anthrax toxin receptor mRNA expression in Raw264.7 macrophage as determined by RT-PCR. In FIG. 1, total RNA was isolated from Raw264.7 cells and Superscript III reverse transcriptase was used to synthesize cDNA. TEM8, CMG2, and GADPH cDNA amplification was optimized by varying annealing temperatures ranging from 55-68° C.

Figure 2A:
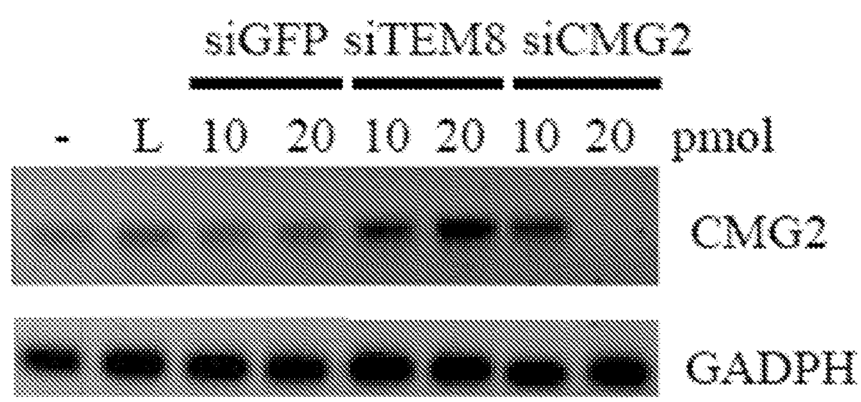

Assessment of anthrax LeTx toxicity in CMG2-silenced cells. First, the optimal amount of targeted siRNA needed to specifically and effectively silence CMG2 transcript expression was determined. These studies were performed in 24-well culture plates so samples would be sufficient for subsequent total RNA extraction. Cells were mock-transfected or transfected with RNAiMAX reagent, siGFP or siTEM as non-specific siRNA controls, and CMG2. RT-PCR analyses revealed that only 20 pmol of siCMG2 specifically and effectively silenced CMG2 mRNA expression (FIG. 2A). RT-PCR analyses using GADPH as a housekeeping gene were performed in parallel and results are also shown (FIG. 2A).

Figure 2B:
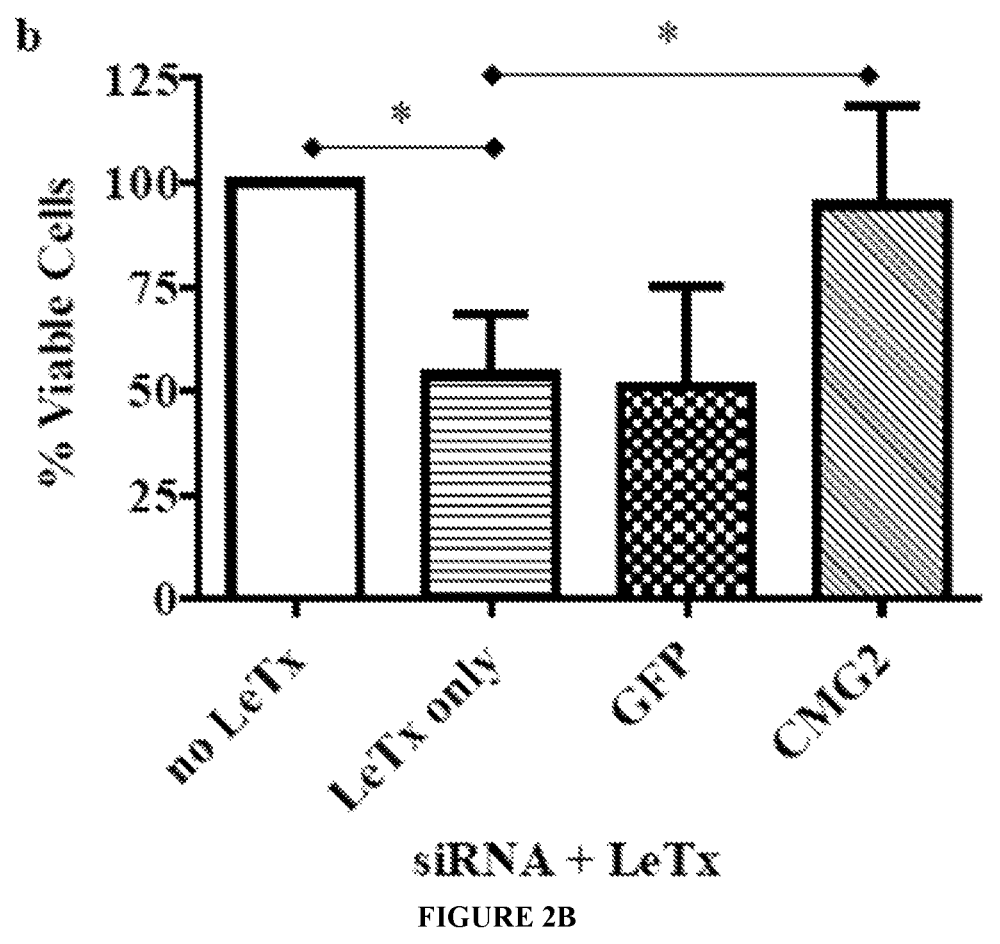

Next, it was determined if CMG2-silenced Raw 264.7 cells were protected against LeTx. Cell viability was assessed following LeTx treatments using a colorimetric, MTT assay in 96-well culture plates (FIG. 2B). Cells that were treated with LeTx alone (LeTx only) were 54% viable when compared to cells not treated with toxin. To control for non-specific siRNA effects, GFP-targeted siRNAs were used to treat cells and as expected, cell viability after toxin treatment was similar to cells that were treated with LeTx only (51%). In contrast, cells treated with CMG2-targeted siRNAs were 95% viable. Thus, specific silencing of CMG2 via targeted siRNAs offered almost complete protection against LeTx. Furthermore, the groups tested were significantly different as determined by two-tailed, one-way ANOVA ($p=0.0033$). Moreover, Dunnett post-hoc comparisons of each group to the LeTx only group revealed that the differences in cell viability between the CMG2-silenced group and the LeTx only group were statistically significant ($p<0.05$).

FIGS. 2A and 2B show that siRNA-targeted silencing of CMG2 and evaluation of anthrax LeTx toxicity. In FIG. 2A, Raw264.7 cells were cultured in 24-well plates and treated as follows: 1) untransfected (−), 2) RNAiMAX alone (L), 3) siGFP 10 and 20 pmol, 4) siTEM8 10 and 20 pmol, and 4) siCMG2 10 and 20 pmol (see Table 2 for sequences). Total RNAs from these cells were isolated after 48 hours and RT-PCR was performed to amplify CMG2 and GADPH fragments. In FIG. 2B, Raw 264.7 cells were cultured in 96-well plates and were transfected twice with 5 pmol siGFP or siCMG2, or mock-transfected. The cells were challenged with anthrax LeTx 48 hours after that last transfection. MTT assays were used to evaluate cell viability. Data were normalized to cell viability controls (no LeTx) in each experiment. The mean+standard deviation (S.D.) of four experiments, performed in triplicates, is shown for all groups. One-way ANOVA revealed the groups to be significantly different ($p=0.0033$) and Dunnett post-hoc comparisons to mock-transfected, LeTx treated cells (LeTx only) were performed (*$p<0.05$).

Figure 3:
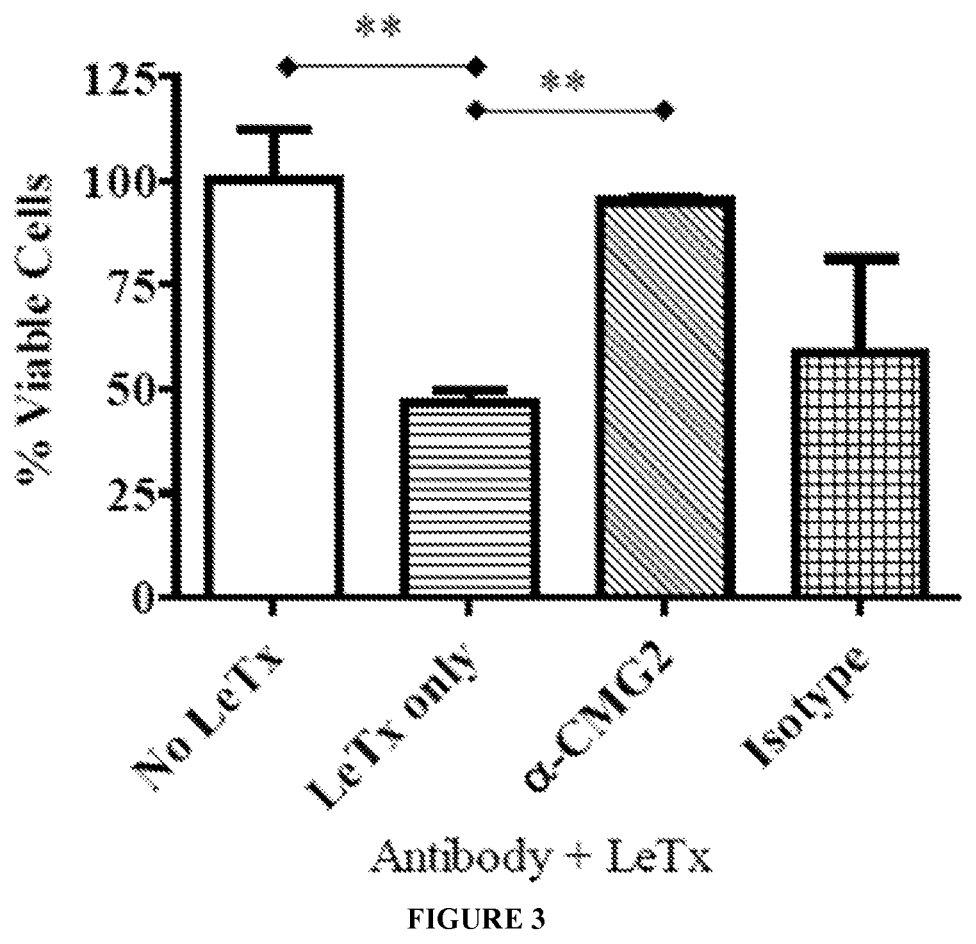

Antibody-blocking of CMG2. A CMG2-specific antibody-blocking assay was used to verify that the unavailability of CMG2 in Raw 264.7 led to the inability of LeTx to induce cytoxicity. The anti-CMG2 goat polyclonal antibody from Abcam (ab101711) was chosen for this assay because it was raised against a peptide sequence: (SEQ ID NO.: 25) HEGLKLANEQIQK, found within the anthrax toxin-binding region (NP_477520.2; NP_001139266.1) and reactive to human, mouse, and rat species. As a negative control, a goat anti-mouse IgG2a antibody was used in this assay. As before, addition of LeTx to Raw 264.7 cells lead to an approximate 50% reduction in cell viability as compared to cells not treated with toxin (FIG. 3). Cells treated with goat anti-mouse IgG2a were also susceptible to LeTx and were only 58% viable. In contrast, cells treated with anti-CMG2 antibody were 95% viable, and thus protected from toxicity.

FIG. 3 shows the evaluation of anthrax LeTx toxicity to Raw 264.7 cells in the presence of anti-CMG2 antibody. Anti-CMG2 or an isotype control antibodies were allowed to bind to Raw 264.7 cells prior to addition of LeTx. MTT assays were used to evaluate cell viability. Data were normalized to cell viability controls (no LeTx) for the experiment performed in triplicates. The mean+S.D. is shown for all groups. One-way ANOVA revealed the groups to be significantly different (p=0.0022) and Dunnett post-hoc comparisons to cells treated with LeTx only were performed (**p<0.01).

Using the present invention murine macrophages were significantly protected from LeTx-induced cell death by silencing CMG2 transcript expression via targeted siRNA therapy. These observations were further substantiated using anti-CMG2 antibodies to block the PA-binding domain of CMG2, which also resulted in protection in murine macrophages against LeTx. Thus, CMG2-targeted siRNAs, and even TEM8-targeted siRNAs, may have therapeutic applications in patients infected with anthrax. Although CMG2 as an anthrax toxin receptor was the focus of this study, it would be beneficial to conduct studies to test if TEM8 can be effectively silenced using specific siRNAs, and if this silencing would lead to protection against LeTx.

Other cell types susceptible to the effects of anthrax toxins include human lung epithelial cells[11] and endothelial cells based on loss of barrier function as measured in vitro. LeTx may also induce apoptosis in human endothelial cells. These observations are supported in vivo in mice with measured vascular leakage following administration of LeTx, and in human inhalational anthrax cases as pleural effusions are a common manifestation[1]. Furthermore, anthrax toxins also suppress immune function in monocytes, macrophage, dendritic cells, B lymphocytes, and T lymphocytes. Thus, it would be important to evaluate if CMG2 or TEM8-targeted siRNA therapy would also aid in countering the effects of anthrax toxins on these cell types.

Finally, using CMG2 or TEM8-targeted RNAi can also be conducted in a murine model of pulmonary anthrax. In vivo, these treatments can be used to provide protection against lethality when used prior to anthrax spore infection, early on during infection, or in later stages of infection.

Cell Culture:

Raw 264.7 (TIB-71, ATCC, Manassas, Va.) were maintained in DMEM (Life Technologies, Grand Island, N.Y.) supplemented with 10% heat-inactivated fetal bovine serum (Sigma-Aldrich, St. Louis, Mo.), 100 U penicillin, and 100 μg streptomycin (complete-DMEM).

siRNA Transfections:

Initial experiments were performed with Raw 264.7 cells seeded in 24-well culture plates at $2\times10^5$ cells per well in 0.5 ml total volume of antibiotic-free DMEM-10% FBS one day prior to transfection with siRNAs. siRNAs targeted to TEM8 (siTEM8) and CMG2 (siCMG2) were purchased from Santa Cruz Biotechnology, Inc (sc-40201 and sc-60232, respectively, Santa Cruz, Calif.). GFP siRNA (siGFP, sense-strand 5' GGCAUCAAGUAUCGGAAGAdTdT-3' (SEQ ID NO.: 26) was custom-ordered from Life Technologies. The siGFP was used as an irrelevant, control siRNA for our studies as the Raw 264.7 cells used did not contain the GFP gene. All siRNAs were delivered to Raw 264.7 cells using Lipofectamine RNAiMax reagent (Life Technologies) as per manufacturer's protocol. Later experiments were down-scaled to a 96-well format, with $1.25\times10_4$ cells seeded per well in 0.1 ml total volume of antibiotic-free medium. In these studies, Raw 264.7 cells were transfected with siRNAs one day after seeding, incubated for 48 hours, transfected again with 48-hour incubation, and challenged with LeTx.

TABLE 1

List of siRNAs

| Target | Mouse siRNA | Human siRNA |
|---|---|---|
| TEM8 | sc-40201, from Santa Cruz Biotechnology | sc-44144, from Santa Cruz Biotechnology |
| CMG2 | sc-60232, from Santa Cruz Biotechnology | sc-60231, from Santa Cruz Biotechnology |

LeTX Challenge and Cell Viability Assay:

LeTx solutions were prepared by incubating 320 μg/ml recombinant LF (List Biologicals Laboratories, Inc., Campbell, Calif.) in PBS for 10 minutes. Recombinant PA (List Biologicals Laboratories) was then added to 480 μg/ml and incubated for another 10 min. LF+PA (LeTx) solutions were then added to Raw 264.7 cells in 96-well plates at 100 μl/well and were incubated for 7 hours at 37° C. and 5% $CO_2$. Some cells were incubated with 100 μl/well PBS instead of LeTx and were used as viable-cell control samples. Following toxin treatments, a thiazolyl blue tetrazolium bromide (MTT) colorimetric assay was used to assess cell viability as described by Twentyman et al[16], with some modification. Briefly, 20 μl of MTT was added to each well and incubated for 2 hours at 37° C. and 5% $CO_2$. Then, the medium was carefully removed and 200 μl/well of dimethyl sulfoxide was added to solubilize the formazan crystals formed. The absorbance was read at 570 nm using the PowerWave XS2 (BioTek, Winooski, Vt.). Readings were normalized to viable-cell control samples for each experiment.

Antibody Blocking of CMG2 Receptors to Inhibit LeTx Toxicity:

Raw 264.7 cells were seeded at $1.25\times10_5$ cells/well in 100 μl/well of complete-DMEM and incubated overnight. The cells were then treated with 1 μg/ml goat anti-CMG2 polyclonal antibody (ab101711, Abcam, Inc., Cambridge, Mass.) or goat anti-mouse IgG2a (Bethyl Laboratories, Inc., Montgomery, Tex.) as negative control for 30 minutes on ice to allow for binding. LeTx challenge followed by assessment of cell viability proceeded as described above.

Reverse Transcription Polymerase Chain Reaction:

RNA was isolated from cells cultured in 24-well plates using QiaShredder and RNeasy Mini kits from Qiagen (Valencia, Calif.). Superscript III reverse transcriptase (Life Technologies) was used for first-strand cDNA synthesis from 0.5 μg total RNA per sample. Murine TEM8 (258 bp), CMG2 (364 bp), and GADPH (239 bp) fragments were then amplified for 36 cycles using specific primers as described by Young et al[9].

Statistical Analyses:

GraphPad Prism Version 5.04 was used to perform statistical analyses. Two-tailed, one-way, analysis of variance (ANOVA) was performed between groups and was followed by Dunnett's multiple comparison tests. A p-value of less than 0.05 was considered significant.

TABLE 2 siRNA Sequences

| siRNA (Catalog #) | Duplex | SEQ ID NO: | Duplex Sequences |
|---|---|---|---|
| si-mCMG2 | A | 1 | Sense: GUGUGACAGUGUAUCUUCAtt |
| (sc-60232) | | 2 | Antisense: UGAAGAUACACUGUCACACtt |
| | B | 3 | Sense: CGACAUGAGAGGUGAUGAAtt |
| | | 4 | Antisense: UUCAUCACCUCUCAUGUCGtt |
| | C | 5 | Sense: GAAGGAAAUAGCUCAGAUAtt |
| | | 6 | Antisense: UAUCUGAGCUAUUUCCUUCtt |
| si-hCMG2 | A | 7 | Sense: GAAGAACCUUUGCCUACUAtt |
| (sc-60231) | | 8 | Antisense: UAGUAGGCAAAGGUUCUUCtt |
| | B | 9 | Sense: CUACCUUGGUUAUGAUUCAtt |
| | | 10 | Antisense: UGAAUCAUAACCAAGGUAGtt |
| | C | 11 | Sense: GAACUGGUAUAGACAAUGAtt |
| | | 12 | Antisense: UCAUUGUCUAUACCAGUUCtt |
| si-mTEM8 | A | 13 | Sense: CCACAGUAGAUGCCUCUUAtt |
| (sc-40201) | | 14 | Antisense: UAAGAGGCAUCUACUGUGGtt |
| | B | 15 | Sense: GCAACCUACUAAUGAUUCAtt |
| | | 16 | Antisense: UGAAUCAUUAGUAGGUUGCtt |
| | C | 17 | Sense: GAACCAAGAUGCUGGUGUUtt |
| | | 18 | Antisense: AACACCAGCAUCUUGGUUCtt |
| si-hTEM8 | A | 19 | Sense: GGAUUUGACCUGUACUUCAtt |
| (sc-44144) | | 20 | Antisense: UGAAGUACAGGUCAAAUCCtt |
| | B | 21 | Sense: CCACUGGAAUGAAAUCUAUtt |
| | | 22 | Antisense: AUAGAUUUCAUUCCAGUGGtt |
| | C | 23 | Sense: GGAACAGUUGGCUCACAAAtt |
| | | 24 | Antisense: UUUGUGAGCCAACUGUUCCtt |

All siRNAs were purchased from Santa Cruz Biotechnology and each consists of 3 pooled siRNA duplexes.
Note:
Sequences are 5' to 3'

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as “about” may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The invention claimed is:

1. A method of treating an anthrax infection in a subject in need of such treatment comprising the steps of:

providing a subject in need of treatment for an anthrax infection;

providing to the subject an effective amount of an siRNA that targets a cell surface expression of a capillary morpho-genesis protein 2 CMG2 cell surface protein to reduce an anthrax toxin binding to one or more cells in the subject.

2. The method of claim 1, wherein the anthrax infection is in the respiratory tract.

3. The method of claim 1, wherein the anthrax infection is in a cutaneous anthrax infections.

4. The method of claim 1, wherein the anthrax infection is of the gastrointestinal tract.

* * * * *

SEQUENCE LISTING

<160> NUMBER OF SEQ ID NOS: 26

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
gugugacagu guaucuucat t 21

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
ugaagauaca cugucacact t 21

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
cgacaugaga ggugaugaat t 21

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
cgacaugaga ggugaugaat t 21

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
gaaggaaaua gcucagauat t 21

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
uaucugagcu auuuccuuct t 21

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
gaagaaccuu ugccuacuat t 21

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
uaguaggcaa agguucuuct t 21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
cuaccuuggu uaugauucat t 21

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
ugaaucauaa ccaagguagt t 21

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
gaacugguau agacaaugat t 21

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
ucauugucua uaccaguuct t 21

-continued

<210> SEQ ID NO 13
<211> LENGTH: 21
<212> TYPE: DNA
<213> ORGANISM: Artificial Sequence
<220> FEATURE:
<223> OTHER INFORMATION: Synthetic primer

<400> SEQUENCE: 13
ccacaguaga ugccucuuat t 21

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
uaagaggcau cuacuguggt t 21

<210> SEQ ID NO 15
<211> LENGTH: 21
<212> TYPE: DNA
<213> ORGANISM: Artificial Sequence
<220> FEATURE:
<223> OTHER INFORMATION: Synthetic primer

<400> SEQUENCE: 15
gcaaccuacu aaugauucat t 21

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
ugaaucauua guagguugct t 21

<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
gaaccaagau gcugguguut t 21

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
gaaccaagau gcugguguut t 21

<210> SEQ ID NO 19
<211> LENGTH: 21
<212> TYPE: DNA
<213> ORGANISM: Artificial Sequence
<220> FEATURE:
<223> OTHER INFORMATION: Synthetic primer

<400> SEQUENCE: 19
ggauuugacc uguacuucat t 21

<210> SEQ ID NO 20
<211> LENGTH: 21
<212> TYPE: DNA
<213> ORGANISM: Artificial Sequence
<220> FEATURE:
<223> OTHER INFORMATION: Synthetic primer

<400> SEQUENCE: 20
ugaaguacag gucaaaucct t 21

<210> SEQ ID NO 21
<211> LENGTH: 21
<212> TYPE: DNA
<213> ORGANISM: Artificial Sequence
<220> FEATURE:
<223> OTHER INFORMATION: Synthetic primer

<400> SEQUENCE: 21
ccacuggaau gaaaucuaut t 21

<210> SEQ ID NO 22
<211> LENGTH: 21
<212> TYPE: DNA
<213> ORGANISM: Artificial Sequence
<220> FEATURE:
<223> OTHER INFORMATION: Synthetic primer

<400> SEQUENCE: 22
auagauuuca uuccaguggt t 21

<210> SEQ ID NO 23
<211> LENGTH: 21
<212> TYPE: DNA
<213> ORGANISM: Artificial Sequence
<220> FEATURE:
<223> OTHER INFORMATION: Synthetic primer

<400> SEQUENCE: 23
ggaacaguug gcucacaaat t 21

<210> SEQ ID NO 24
<211> LENGTH: 21
<212> TYPE: DNA
<213> ORGANISM: Artificial Sequence
<220> FEATURE:
<223> OTHER INFORMATION: Synthetic primer

<400> SEQUENCE: 24
uuugugagcc aacuguucct t 21

<210> SEQ ID NO 25
<211> LENGTH: 21
<212> TYPE: DNA
<213> ORGANISM: Artificial Sequence
<220> FEATURE:
<223> OTHER INFORMATION: Synthetic primer

<400> SEQUENCE: 25
ggcaucaagu aucggaagat t 21

<210> SEQ ID NO 26

-continued

```
<211> LENGTH: 13
<212> TYPE: PRT
<213> ORGANISM: Artificial Sequence
<220> FEATURE:
<223> OTHER INFORMATION: Synthetic peptide

<400> SEQUENCE: 26

His Glu Gly Leu Lys Leu Ala Asn Glu Gln Ile Gln Lys
1               5                   10
```